United States Patent [19]

Worrell

[11] 4,158,894
[45] Jun. 26, 1979

[54] PATELLAR PROSTHESIS AND METHOD OF IMPLANTING THE SAME

[76] Inventor: Richard V. Worrell, 2 Cliffmount Dr., Bloomfield, Conn. 06002

[21] Appl. No.: 886,079

[22] Filed: Mar. 13, 1978

[51] Int. Cl.$^2$ ............................................. A61F 1/24
[52] U.S. Cl. ..................................... 3/1.91; 128/92 C
[58] Field of Search .................... 3/1.9–1.913; 128/92 C

[56] References Cited

U.S. PATENT DOCUMENTS

| 3,806,961 | 4/1974 | Muller | 3/1.913 |
| 3,878,566 | 4/1975 | Bechtol | 3/1.91 |
| 3,886,599 | 6/1975 | Schlein | 3/1.91 |
| 3,927,423 | 12/1975 | Swanson | 3/1.91 |
| 3,964,106 | 6/1976 | Hutter, Jr. et al. | 3/1.911 |
| 4,007,495 | 2/1977 | Frazier | 3/1.91 |
| 4,069,518 | 1/1978 | Groth, Jr. et al. | 3/1.91 |

FOREIGN PATENT DOCUMENTS 2154338  5/1973  Fed. Rep. of Germany ............ 3/1.911

OTHER PUBLICATIONS

"A Comparison of Patellectomy with Prosthetic Replacement of the Patella", by R. V. Worrell, Clinical Orthopaedics and Related Research, No. III, Sep. 1975, pp. 284–289.

"Some Aspects of Prosthetic Replacement of the Patella", by R. V. Worrell, Orthopaedic Review, vol. V, No. II, Nov. 1976, pp. 39–42.

*Primary Examiner*—Ronald L. Frinks

[57] ABSTRACT

A patellar prosthesis has a hollow body portion providing a convex articulating surface on one side and a mounting chamber on its opposite side which provides a peripheral seating rim. An anchoring stem is attached to the body portion within the mounting recess and extends in a direction outwardly thereof and terminates in a flat base plate. The stem is formed of a pair of webs intersecting at a right angle to each other. The hollow body and cruciate cross section stem construction provides a light weight prosthesis which can be securely implanted on a patella which has been resected to provide a raised land portion having a central recess by fitting the seating rim on the raised land. A surgical cement is employed to help secure the prosthesis in place.

19 Claims, 11 Drawing Figures

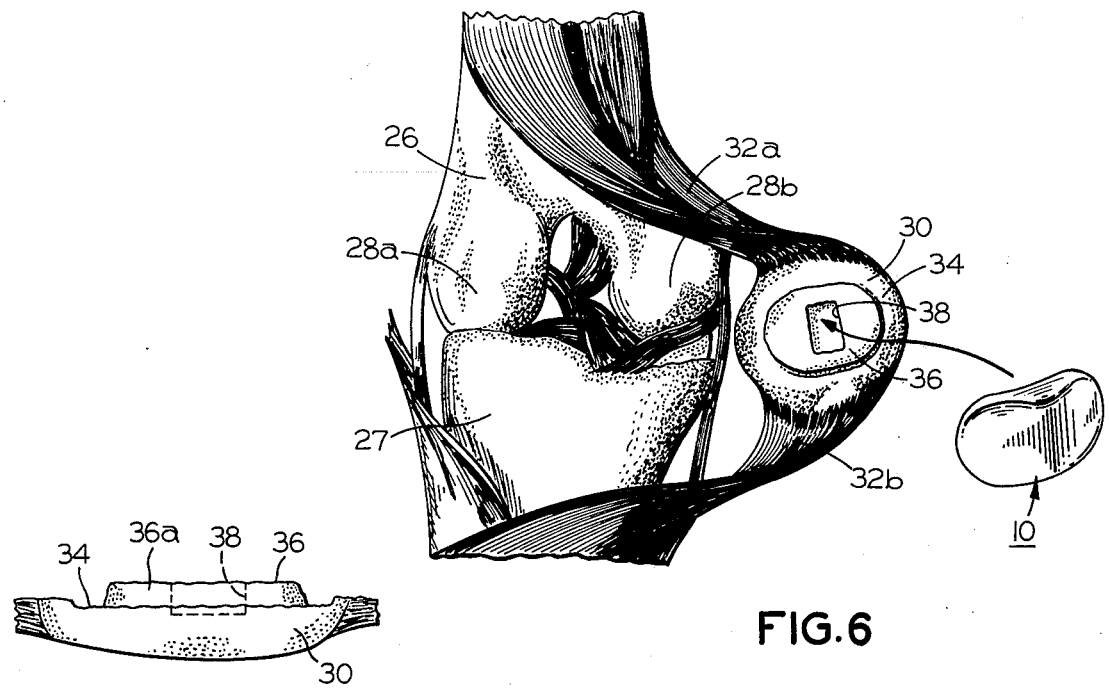
FIG.6
FIG.6A
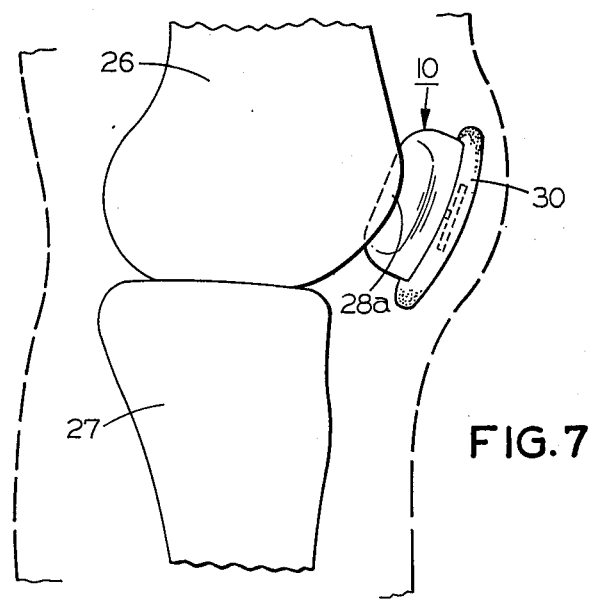
FIG.7

PATELLAR PROSTHESIS AND METHOD OF IMPLANTING THE SAME

BACKGROUND OF THE INVENTION

The present invention pertains to a patellar prosthesis and to a method of surgically implanting the same.

Prosthetic replacement of the patella has been known for some time. The patella is a small triangular shaped bone, commonly referred to as the kneecap, and has a posterior surface which has a transversely extending crest which divides the surface into a medial and a lateral facet which bear, respectively, on the femoral condyles. Trauma, degenerative changes or disease may cause this natural articulating surface to degenerate causing severe pain, and/or immobility of the knee joint. In such cases, particularly where more conservative methods of treatment fail, the implantation of a prosthesis to replace the degenerated natural articulating surface of the patella with an artificial surface is indicated.

Such prostheses are known in the art. For example, U.S. Pat. No. 3,927,423 discloses a patella implant formed of a resilient material, silicone rubber, which is sutured in place onto a flat resection of the patella posterior surface to provide an artificial articulating surface.

The use of a rigid patellar prosthesis is also known. For example, see the article "*Some Aspects of Prosthetic Replacement of The Patella*" by the inventor of the present invention in *Orthopaedic Review*, Volume V, No. 11, November 1976, pages 39-42. At page 40 of the cited article, there is shown a prior patellar prosthesis which comprises a rigid body having one side providing a convex articulating surface and an opposite side which is recessed somewhat and in which a stem of generally rectangular cross section is positioned. The stem extends outwardly and terminates in an enlarged cross section portion. Such prostheses are rigid, usually being made of a stainless steel for strength and durability. This results in one difficulty encountered with the prosthesis illustrated in the article, in that the thickness of the body portion and stem results in a device which is quite heavy for its size. As a consequence, patients in whom it was implanted required a good quadri ceps muscular reserve in order to be able to manipulate the knee joint with facility.

Another shortcoming of the described prosthesis is that the flat or planar configuration of the seating rim in side profile and the generally rectangular cross section of the anchoring stem failed to adequately secure the implanted prosthesis against shifting and/or rotation. This problem was aggravated by the heaviness of the device.

It is accordingly an object of the present invention to provide a novel patellar prosthesis of rigid construction which is light in weight and which may be implanted in the patella posterior surface in a manner in which it is secured against shifting or rotation.

It is another object of the present invention to provide a light weight patellar prosthesis of novel design and a method of implanting the same.

Other objects and advantages of the present invention will become apparent from the following description thereof.

SUMMARY OF THE INVENTION

In accordance with the present invention there is provided a patellar prosthesis adapted to be surgically implanted on the resected bone structure of a patella. The prosthesis comprises a body portion having a posterior side providing a convex articulating surface having a medial facet and a lateral facet divided by a transversely extending crest, and an anterior side providing a concave surface defining a mounting chamber having a peripheral seating rim thereabout, the seating rim being arcuately concave in longitudinally extending profile. An anchoring stem of cruciate cross section has one end affixed to the anterior side of the body member within the mounting chamber, and an opposite end. The anchoring stem extends in a direction outwardly of the mounting chamber. A base plate is on the opposite end of the anchoring stem and is spaced from the body portion on the anterior side thereof, the base plate providing a seating surface facing away from the body portion.

In one aspect of the invention, the anchoring stem is comprised of at least a pair of intersecting web plates, one of the web plates being disposed longitudinally of the body portion and the other of the web plates being disposed transversely of the body portion to provide the aforesaid cruciate cross section of the stem.

The invention provides for an embodiment wherein the anchoring stem is comprised of two intersecting web plates and the base plate is comprised of a plate member disposed perpendicularly to the web plates and has a generally planar top surface which is disposed outwardly of the mounting chamber to provide a clearance between the seating rim and the plane in which the top surface lies. The base plate seating surface may extend longitudinally for at least about one quarter of the overall longitudinal length of the body portion and transversely for at least about one half of the overall transverse width of the body portion, but terminates short of being coextensive with the peripheral seating rim whereby to provide an annular clearance between the periphery of the base plate and the seating rim. The seating rim has opposite transversely extending segments which are arcuately convex in transversely extending profile. The base plate has a generally planar top surface which is disposed outwardly of the mounting chamber to provide a clearance between the seating rim and the plane in which the top surface lies.

Generally, the patellar prosthesis of the invention may be considered to have a cup-shaped body portion comprised of a wall member having its maximum thickness in the region of the crest, and having a smoothly tapering longitudinal cross section with the thinnest portions of the wall member occurring in the central portions of the lateral and medial facets.

In accordance with the invention there is also provided, in a method of implanting a patellar prosthesis on a human patella, the steps comprising: exposing the posterior surface of a human patella by separating the patella from the femoral condyles; resecting the posterior surface to provide thereon a raised land portion having a central recess having a bottom floor formed therein; applying a cement to the resected surface; mounting on the resected surface a patellar prosthesis having:

(1) a body portion providing a convex articulating surface on one side and a concave mounting chamber on its other side, and (2) an anchoring stem having one end supported within the mounting recess and extending in a direction outwardly thereof, by inserting the stem into the central recess and fitting the mounting chamber over the raised land portion to adhere the prosthesis thereto; and replacing the patella in its natural orientation with the articulating surface of the prosthesis bearing on the femoral condyles.

BRIEF DESCRIPTION OF THE DRAWINGS

FIG. 6 is a frontal view rendition of a human knee joint in the standing position showing the patella twisted out of position away from the joint to expose its posterior surface which is shown resected in preparation for mounting of the prostheses of FIG. 1 thereon;

FIG. 6A is a transverse side view of the resected patella of FIG. 6; and

FIG. 7 is a schematic rendition of a side view of a human knee joint in standing position illustrating the relative position of the knee joint and patella to the implanted prosthesis.

FIGS. 1–5 of the drawings are drawn to scale, approximately twice the actual side of the illustrated prosthesis, and show the actual configuration of the preferred embodiment. Final polishing and grinding may round edges, etc. somewhat more than shown in the drawings.

DESCRIPTION OF THE PREFERRED EMBODIMENT

Figure 2:
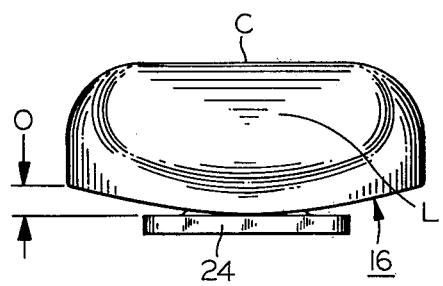
FIG. 2 is a transverse end view in elevation of the lateral facet end of the prosthesis of FIG. 1.
Figure 3:
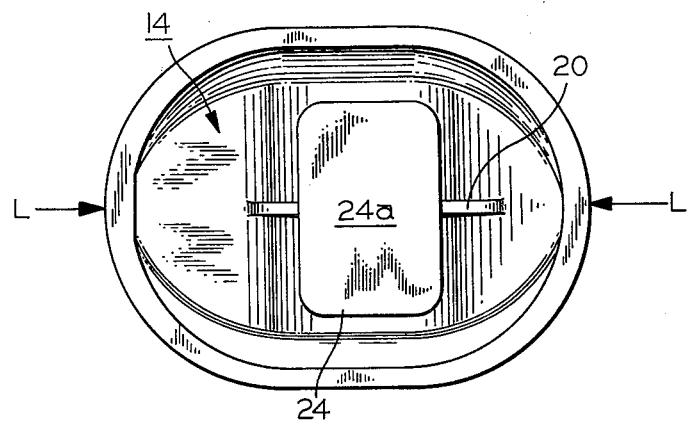
FIG. 3 is a plan view of the anterior surface of the prosthesis of FIG. 1.
Figure 4:
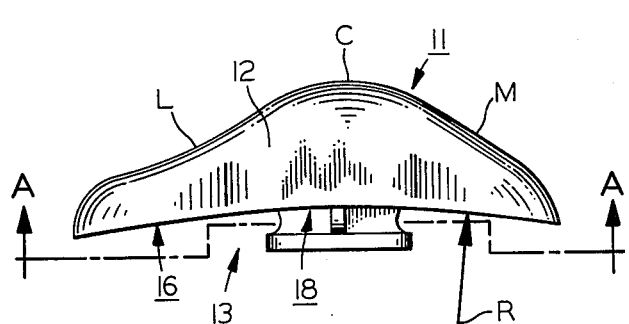
FIG. 4 is a longitudinal side view in elevation of the prosthesis of FIG. 1.

Referring generally to FIGS. 1–5, a prosthesis in accordance with the present invention is generally indicated at 10 (FIG. 1) and has a body portion 12 having a posterior side 11 and an opposite anterior side 13, generally indicated in FIG. 4. Posterior side 11 provides a convex articulating surface S (FIG. 1) having a medial facet M and a lateral facet L which are separated by a transversely extending crest C. Medial facet M and lateral facet L are longitudinally adjacent to one another, that is, they are spaced from one another along the longitudinal axis of body portion 12. Articulating surface S is highly polished to a smooth, mirror like finish. Preferably, prosthesis 10 is made of an integral metal stainless steel casting for strength, durability and inertness.

As will be recognized by those skilled in the art, articulating surface S simulates the shape of the posterior, i.e., articulating, surface of a healthy, well formed human patella. The patella is a roughly triangular shaped small bone whose articulating surface bears on the femoral condyles and is held in place by connective tissue connecting it to the muscular system.

Figure 1:
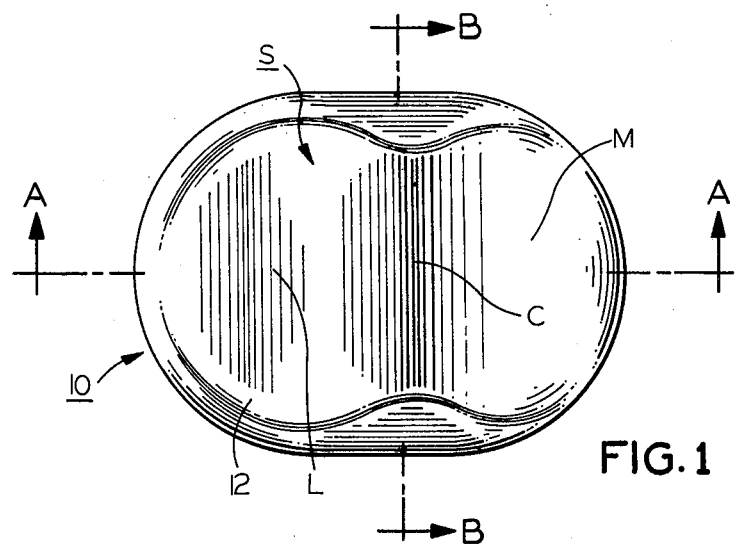
FIG. 1 is a plan view of the posterior surface of one embodiment of a pateller prosthesis in accordance with the present invention.
Figure 1A:
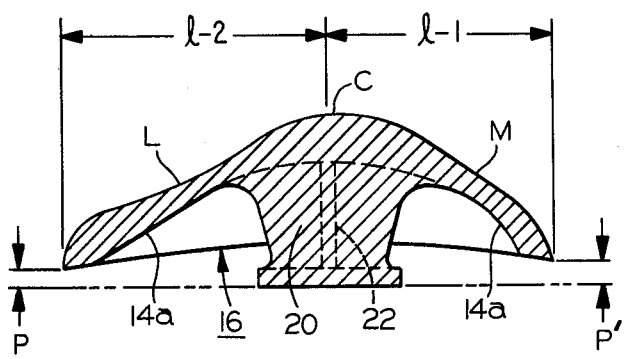
FIG. 1A is a longitudinal section view in elevation taken along line A—A of FIG. 1.
Figure 4A:
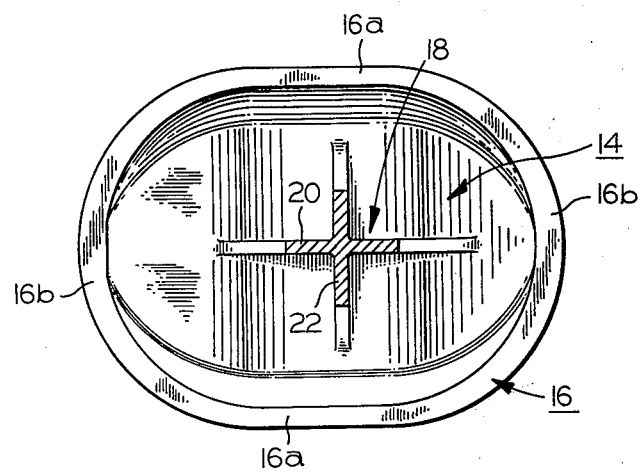
FIG. 4A is a section plan view taken along line A—A of FIG. 4.

Anterior side 13 of the body portion 12 is recessed to provide a mounting chamber generally indicated at 14 which provides the prosthesis with a generally cup-shaped, hollow overall configuration. Mounting chamber 14 has a surface 14a and is configured to provide a peripheral seating rim thereabout, generally indicated at 16 and best seen in FIGS. 3 and 4A. Peripheral seating rim 16 (FIG. 4A) has a pair of opposed generally longitudinal segments 16a and a pair of opposed generally transverse segments 16b defining its approximately oval shaped configuration. As shown in FIGS. 1A and 4, the opposite longitudinal segments 16a of seating rim 16 are arcuately concave in longitudinally extending profile. Peripheral seating rim 16 thus is generally arcuately concave in longitudinal extending profile and, overall, has a generally saddle shaped ring configuration.

Figure 1B:
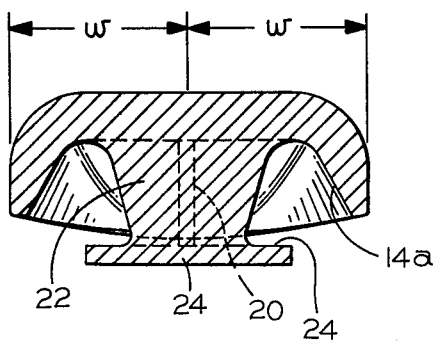
FIG. 1B is a transverse section view in elevation taken along line B—B of FIG. 1.

An anchoring stem 18 has one end thereof affixed to body portion 12 within mounting chamber 14. Anchoring stem 18 is seen to be of cruciate cross section (FIG. 4A) being comprised of a pair of web plates 20, 22 which intersect along the longitudinal center axis of stem 18. Web 20 extends longitudinally relative to body portion 12 and web 22 extends transversely relative to body portion 12. In the illustrated embodiment, webs 20 and 22 are disposed at a right angle to each other. The profile of longitudinally extending web 20 is best seen in the section view of FIG. 1A and the profile of transversely extending web 22 is best seen in FIG. 1B. Webs 20 and 22 are blended smoothly into the inner surface 14a of mounting chamber 14 and extend for at least a major portion of the overall width W and length L, respectively of prosthesis 10.

A base plate 24 is attached to the distal end of anchoring stem 18. As shown in FIG. 3, base plate 24 is generally rectangular in plan view but has rounded corners and provides a seating surface 24a spaced from anterior side 13 of body portion 12 and adapted to be received within a recess formed in the resected patella bone, as described more fully hereinbelow. Base plate 24 extends generally parallel to the longitudinal axis of body portion 12, which may be considered to coincide with section line A—A in FIG. 1 and pass through the center of gravity of body portion 12. Seating surface 24a lies in a plane disposed generally parallel to the longitudinal axis of body portion 12. The peripheral of base plate 24 terminates short of the inside periphery of seating rim 16 to provide a clear annular entryway into mounting chamber 14 between the periphery of base plate 24 and seating rim 16. The annular clearance longitudinally of each side of base plate 24 should be at least about three-quarters of the longitudinal length of base plate 24; the annular clearance transversely on each side should be at least about one-fifth of the transverse width of base plate 24 to allow sufficient clear room for reception of the resected bone structure into chamber 14.

The length of base plate 24 is at least about one quarter of the longitudinal length L (indicated by the dimension arrows L in FIG. 3) of prosthesis 10. The width of base plate 24 is at least about one-half of the width W (indicated by dimension arrows W in FIG. 5) of prosthesis 10.

However, as noted above, base plate 24 terminates short of being coextensive with seating rim 16 to provide ample annular clearance. The minimum dimensions of base plate 24 provide a seating surface 24a which is large enough to provide stable and secure seating of the prosthesis. Stem 18 and its base plate 24 are disposed generally centrally of prosthesis 10, between the medial and lateral facets M, L, i.e., at the crest C.

As shown in FIG. 1A, seating surface 24a is disposed outwardly of mounting chamber 14, extending outwardly by a distance P of the outermost portion of seating rim 16 at the lateral facet end of body portion 12, and outwardly by a distance P' beyond the outermost portion of seating rim 16 at the medial facet end of body portion 12.

Base plate 24 has a top surface 24b (FIG. 5) which provides an effectively horizontally disposed (as viewed in the drawings) surface substantially equal to that of seating surface 24a except for that cross-shaped portion thereof to which anchor stem 18 is joined. As indicated in FIG. 2, a clearance O exists between top surface 24b and seating rim 16. The illustrated dimension O indicates the maximum clearance, but it is seen in the drawing that there is at least some clearance between top surface 24b and seating rim 16 for practically the entire periphery of rim 16.

Referring again to FIGS. 1A and 1B, it is seen that webs 20, 22 show a tapering profile, being widest at the point where they connect to body portion 12 and tapering to a narrower portion where they connect to base plate 24. Body portion 12 is seen to be comprised essentially of a wall member which has a smoothly tapering concave longitudinal profile as shown in FIG. 1A. As shown in FIG. 1B, in transverse profile the wall member comprising body portion 12 has a generally broadly bottomed U-shaped cross sectional profile which tapers to a thinner portion adjacent seating rim 16. Referring again to FIG. 1A, it is seen that the wall member comprising body portion 12 is thickest in the region of the transversely extending crest C and thinnest in the region of the central portions of lateral and medial facets L, M.

It should also be noted that the construction of prosthesis 10 is such that by revolving it 180° about the longitudinal axis of stem 18, the prosthesis is adapted to be implanted in either the right or left human patella.

While the patella may be made to any appropriate size, the following dimensions have been found to be suitable for a patella adapted for substantially universal use as a prosthesis for adults:

| | |
|---|---|
| Longitudinal length of base plate 24: | 0.480 inches |
| Transverse width of base plate 24: | 0.680 inches |
| Thickness of base plate 24: | 0.060 inches |
| Overall longitudinal length (L) of prosthesis 10: | 1.625 inches |
| Overall transverse width (W) of prosthesis 10: | 1.187 inches |
| Overall thickness (T) of prosthesis 10: | 0.560 inches |
| Radius of curvature (R) of arcuately concave portion of rim 16: | 4.50 inches |
| Thickness of webs 20, 22: | 0.040 inches |
| Distance w (FIG. 1B): | 0.593 inches |
| Distance 1-1 (FIG. 1A): | 0.750 inches |
| Distance 1-2 (FIG. 1A): | 0.875 inches |

Figure 5:
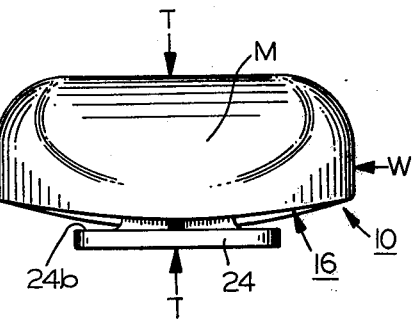
FIG. 5 is a transverse end view in elevation of the medial facet end of the prosthesis of FIG. 1.

FIGS. 3 and 5, as indicated above, illustrate respectively the overall length and width of prosthesis 10 by, respectively, dimension arrows L and W. Dimension arrows T in FIG. 5 illustrate the overall thickness of prosthesis 10. Each dimension is measured at its point of greatest value.

Referring now to FIG. 6, an elevation view of a human knee joint shows the lowermost portion of the femur 26 and the uppermost portion of the tibia 27. The human femur terminates at its lower end in a pair of rounded protuberances comprising femoral condyles 28a, 28b. The patella or kneecap 30 is shown twisted out of position to expose its posterior surface which, in a healthy patella, is crest-shaped to provide a generally convex articulating surface having facets which bear against, respectively, femoral condyles 28a, and 28b. The patella is held in place by connective tissue 32a, 32b joining it to the muscular system. In the drawing, the degree of displacement of the patella is exaggerated for clarity of illustration but the position generally corresponds to that into which the patella is moved in surgery for implantation of the prosthesis. That is, in order to expose the posterior articulating surface of the patella, a long medial parapatellar incision is made and the patella and associated connective tissue is rotated outwardly to expose the posterior surface of the patella. The degenerated or damaged posterior surface is then resected to provide a generally flat surface; and a burr is employed to provide on resected surface 34 a raised land portion 36 (FIGS. 6 and 6A). A central recess 38 is provided in land portion 36. Central recess 38 does not extend entirely through patella 30 but has a bottom floor, unnumbered. "Central" does not mean that it is necessarily precisely geometrically centered in patella 30 or land 34; it merely connotes that recess 38 does not extend to rim 36a of land portion 36.

In practice, a template is provided which corresponds to the corresponding dimensions of prosthesis 10 to guide the surgeon in resecting the posterior surface of the patella to the configuration shown. Prior to commencing the resecting, the crest thickness of the natural patella is measured so that the depth of the resecting may be carried out to an extent sufficient so that the combined thickness of the prosthesis and the remnant of the natural patella is approximately equal to the original thickness of the natural patella.

When the resecting is complete, the prosthesis is implanted in the resected bone with base plate 24 fitting into central recess 38 and seating rim 16 being seated about the outer periphery of land portion 36 upon excised flat surface 34. Thus, land portion 36 is received within mounting chamber 14 and the peripheral upstanding edges 36a of land portion 36 seat against surface 14a along the lip portion thereof adjacent seating rim 16. A suitable surgical cement such as methylmethacrylate is employed on land portion 36 and within recess 38 to firmly secure the prosthesis in place. Further, the soft, spongy inner bone tissue of the resected patella within recess 38 will, to a certain extent, extend within the area provided adjacent the cross section of anchor stem 18, and over top surface 24b of base plate 24. This natural sponginess of resected portions of the bony tissue, together with the entry of the adhesive, provides secure mounting of the prosthesis to the patella. The cruciate cross section of anchoring stem 18 and the reception of base plate 24 within recess 38, together with the engagement of the rim portion of surface 14b by raised land 36, provides secure mounting of the prosthesis, holding it against lateral shifting or rotation.

FIG. 7 shows in a schematic side view of the knee joint, the relative position of the implanted prosthesis 10 in the resected patella 30 relative to femoral condyle 28a of femur 26. The dotted outline generally indicates the outline of the patient's leg in the knee joint area.

The prosthesis of the invention has been successfully employed to restore mobility to knee joints having diseased or damaged patellae. Its relatively light weight does not unduly penalize patients with poor quadriceps muscular reserve. The implanted prosthesis has successfully resisted shifting or rotation. The cruciate, i.e., cross-like or spoked, cross section of the stem and the positioning of a raised land area of bond into the mounting chamber between the arcuately concave seating rim and the stem and base plate cooperate to securely retain the patella. The relatively thin wall construction of the prosthesis, the arcuately concave rim configuration and the cross-web construction of the stem reduce the overall weight as much as possible consistent with satisfactory strength and dimensions. For example, the illustrated preferred embodiment weighs only about one-third as much as that shown in the above-mentioned article in *Orthopaedic Review* and is stable after implantation whereas the earlier model was not. The weight comparison is on the basis of both prosthesis being made of the same material and having the same overall length, width and thickness dimensions.

While the invention has been described with respect to a specific preferred embodiment thereof, it will be appreciated by those skilled in the art that numerous modifications and alterations may be made thereto which are nonetheless within the scope and spirit of the invention. It is intended to include such modification and alterations within the scope of the appended claims.

What is claimed is:

1. A patellar prosthesis adapted to be surgically implanted on the resected bone structure of a patella and comprising;
   (a) a body portion having a posterior side providing a convex articulating surface having a medial facet and a lateral facet divided by a transversely extending crest, and an anterior side providing a concave surface defining a mounting chamber having a peripheral seating rim thereabout, said seating rim being arcuately concave in longitudinally extending profile;
   (b) an anchoring stem of cruciate cross section and having one end affixed to said anterior side of said body member within said mounting chamber and an opposite end, said anchoring stem extending in a direction outwardly of said mounting chamber; and
   (c) a base plate on said opposite end of said anchoring stem and spaced from said body portion on said anterior side thereof, said base plate providing a seating surface facing away from said body portion.

2. The prosthesis of claim 1 wherein said anchoring stem is comprised of at least a pair of intersecting web plates, one of said web plates being disposed longitudinally of said body portion and the other of said web plates being disposed transversely of said body portion to provide said cruciate cross section of said stem.

3. The prosthesis of claim 1 wherein said base plate is comprised of a generally flat plate member.

4. The prosthesis of claim 2 wherein said anchoring stem is comprised of two of said intersecting web plates and said base plate is comprised of a plate member disposed perpendicularly to said web plate.

5. The prosthesis of claim 1 wherein said base plate has a generally planar top surface which is disposed outwardly of said mounting chamber to provide a clearance between said seating rim and the plane in which said top surface lies.

6. The prosthesis of claim 1 wherein said base plate provides a seating surface lying in a plane disposed outwardly of said mounting chamber and of said seating rim.

7. The prosthesis of claim 1 wherein said base plate provides a seating surface which extends longitudinally for at least about one quarter of the overall longitudinal length of said body portion and which extends transversely for at least about one half of the overall transverse width of said body portion but terminates short of being coextensive with said peripheral seating rim whereby to provide an annular clearance between the periphery of said base plate and said seating rim.

8. The prosthesis of claim 1 wherein said seating rim has opposite transversely extending segments which are arcuately convex in transversely extending profile.

9. The prosthesis of claim 1 wherein the various components thereof are integrally formed.

10. The prosthesis of claim 9 formed from an integral metal casting.

11. A patellar prosthesis adapted to be surgically implanted in the resected bone structure of a patella and comprising:
    (a) a generally cup-shaped body portion having a convex articulating surface providing a medial facet and a lateral facet disposed longitudinally adjacent to each other and separated by a transversely extending crest, and an opposite concave surface forming a mounting chamber having a generally saddle shaped peripheral seating rim which is arcuately concave in longitudinally extending profile and arcuately convex in transversely extending profile;
    (b) an anchoring stem of cruciate cross section having one end affixed to said body portion within said mounting recess and extending in a direction outwardly therefrom;
    (c) a base plate at the opposite end of said anchoring stem and spaced from said body portion, said base plate providing a generally planar seating surface facing away from said body portion.

12. The prosthesis of claim 11 wherein said body portion is comprised of a wall member having its maximum thickness in the region of said crest, and having a smoothly tapering longitudinal cross section with the thinnest portions of the wall member occurring in the central portions of said lateral and medial facets.

13. The prosthesis of claim 12 wherein said anchoring stem is comprised of a pair of intersecting web plates, one of said web plates being disposed longitudinally of said body portion and the other of said web plates being disposed transversely of said body portion to provide said cruciate cross section of said stem, and said base plate is comprised of a base member disposed perpendicularly to said web plates at said opposite end of said stem.

14. The prosthesis of claim 13 wherein said base plate has a generally planar top surface which is disposed outwardly of said mounting chamber to provide a clearance between said seating rim and the plane in which said top surface lies, and said seating surface of said base plate extends longitudinally for at least about one quarter of the overall longitudinal length of said body portion and extends transversely for at least about one half of the overall transverse width of said body portion, but terminates short of being coextensive with said peripheral seating rim whereby an annular clearance is provided between the periphery of said base plate and said seating rim.

15. The prosthesis of claim 13 comprising an integral metal casting having a highly polished articulating surface.

16. The prosthesis of claim 15 wherein said web plates comprising said anchoring stem are of tapered configuration, tapering from a wider width where they join said body portion to a narrower width where they join said base plate.

17. In a method of implanting a patellar prosthesis on a human patella, the steps comprising:
  (a) exposing the posterior surface of a human patella by separating the patella from the femoral condyles;
  (b) resecting said posterior surface to provide thereon a raised land portion having a central recess formed therein, said central recess having a bottom floor;
  (c) applying a cement to said resected surface;
  (d) mounting on said resected surface a patellar prosthesis having:
    (1) a body portion providing a convex articulating surface on one side and a concave mounting chamber on its other side, and
    (2) an anchoring stem having one end supported within said mounting recess and extending in a direction outwardly thereof, by inserting said stem into said central recess and fitting said mounting chamber over said raised land portion to adhere said prosthesis thereto; and
  (e) replacing said patella in its natural orientation with said articulating surface of said prosthesis bearing on the femoral condyles.

18. The method of claim 17, wherein said prosthesis further includes a base plate on said stem at the end thereof opposite the end supported within said mounting recess, and said mounting chamber defines a peripheral seating rim which is arcuately concave in longitudinally extending profile, and including inserting said base plate into said central recess and seating it on said bottom floor thereof.

19. The method of claim 18, wherein said anchoring stem is of cruciate cross section, and including the step of filling the space between said anchoring stem and said central recess with said cement.

* * * * *